United States Patent [19]
Lopez et al.

[11] Patent Number: 5,938,702
[45] Date of Patent: Aug. 17, 1999

[54] LOCKING MECHANISM FOR ACETABULAR CUP

[75] Inventors: Jorge Lopez, Oxnard, Calif.; Steve Van der meulen, Zephyr Hills, Fla.

[73] Assignee: Sulzer Orthopedics Inc., Austin, Tex.

[21] Appl. No.: 08/962,163

[22] Filed: Oct. 31, 1997

[51] Int. Cl.⁶ ............................ A61F 2/32; A61F 2/34
[52] U.S. Cl. .................................... 623/22; 623/18
[58] Field of Search ................... 623/22, 18, 2; 128/92

[56] References Cited

U.S. PATENT DOCUMENTS

| | | |
|---|---|---|
| 168,140 | 9/1875 | Collins et al. . |
| 453,285 | 6/1891 | Kneider . |
| 489,258 | 1/1893 | Marks . |
| 492,583 | 2/1893 | Duffie . |
| 909,859 | 1/1909 | Apgar . |
| 1,216,367 | 2/1917 | Rowley . |
| 1,314,136 | 8/1919 | Gaines et al. . |
| 1,370,299 | 3/1921 | Flanagan . |
| 3,863,273 | 2/1975 | Averill ............... 128/92 |
| 4,285,071 | 8/1981 | Nelson ............... 128/92 |
| 4,417,571 | 11/1983 | Nelson ............... 128/92 |
| 4,778,474 | 10/1988 | Homsy ............... 623/22 |
| 5,139,526 | 8/1992 | Skardoutos et al. . |
| 5,181,929 | 1/1993 | Prats ................ 623/23 |
| 5,226,918 | 7/1993 | Silagy et al. . |
| 5,443,519 | 8/1995 | Averill et al. ........... 623/22 |
| 5,458,650 | 10/1995 | Carret et al. ........... 623/22 |
| 5,549,698 | 8/1996 | Averill et al. ........... 623/22 |
| 5,676,704 | 10/1997 | Ries .................. 623/18 |
| 5,725,591 | 3/1998 | DeCarlo, Jr. et al. ...... 623/22 |
| 5,735,901 | 4/1998 | Maumy et al. .......... 623/22 |
| 5,766,260 | 6/1998 | Whiteside ............. 623/22 |

FOREIGN PATENT DOCUMENTS 599365 10/1959 Italy .

OTHER PUBLICATIONS

Michael J. Wentz, Harry E. Rubash, Arun S. Shanbhag; Evaluation of Micromotion of the Inter–Op Acetabular System.

Benjamin I. Rosner, Paul D. Postak, A. Seth Greenwald; Cup/Liner Incongruity of Two Piece Acetabular Designs: Implications in the Generation of Polyethylene Debris.

Primary Examiner—David H. Willse
Assistant Examiner—Suzette J. Jackson
Attorney, Agent, or Firm—Philip S. Lyren

[57] ABSTRACT

An implantable orthopedic prosthesis is provided that includes a shell having a substantially concave inner surface defining a cavity and a substantially annular groove formed therein. The prosthesis further includes a polymeric insert that is positionable within the cavity of the shell, and that has a substantially convex outer surface and a circumferential protrusion projecting therefrom. The protrusion has a substantially trapezoidal cross-section wherein at least one of the sides of the trapezoid is substantially parallel to the axis of symmetry of the insert. The cross-section of the protrusion is substantially congruent to the cross-section of the groove of the shell, and the inner surface of the shell is substantially congruent with a corresponding portion of the outer surface of the insert when the insert is properly positioned within the cavity of the shell.

21 Claims, 5 Drawing Sheets

LOCKING MECHANISM FOR ACETABULAR CUP

BACKGROUND OF THE INVENTION

1. Field of the Invention

The present invention relates generally to implantable prostheses for replacing human skeletal joints, and relates more particularly to an acetabular component of an implantable orthopedic hip prosthesis.

2. Background Information

Implantable orthopedic prostheses, in one form, comprise man-made replacements for the ends and articulating surfaces of the bones of the skeleton. Such prostheses are implanted to repair or reconstruct all or part of an articulating skeletal joint that is functioning abnormally due to disease, trauma, or congenital defect. Among the various articulating skeletal joints of the human body that are eligible to be fitted with implantable orthopedic prostheses, the hip joint is often treated with such prostheses. The hip joint is a major weight bearing joint and degenerates more quickly than some other joints in the event of abnormality. Also, the hip joint plays a critical role in ambulation and quality of life, resulting in great demand for surgical correction of abnormalities.

The human hip joint involves two bones: the femur and the pelvis, each having a smooth articulation surface arranged for articulation against an adjacent articulation surface of the other bone. The femur includes at its proximal extremity a head having a convex, generally spherically contoured articulation surface. The pelvis, in pertinent part, includes an acetabulum having a concave, generally spherically contoured articulation surface. The mutually engaging articulation surfaces of the femur and the pelvis together form, functionally, a ball-and-socket joint.

One or both of the articulation surfaces of the hip joint may fail to perform properly, requiring the defective natural articulation surface to be replaced with a prosthetic articulation surface provided by an implantable prosthesis. To accommodate defects of varying scope, while permitting healthy portions of the hip joint to be conserved, a range of types of orthopedic implants is available. The range extends from total hip prosthesis systems for replacing the articulation surfaces of both the femur and the pelvis, to less comprehensive systems for replacing only the femoral articulation surface. Commonly employed orthopedic hip prostheses include components that fall within one of three principle categories: femoral stems, femoral heads and acetabular cups. A so-called "total" hip prosthesis includes components from each of these categories. The femoral stem replaces the proximal end of the femur and includes a distal stem that is received within the medullary canal at the proximal end of the femur. The femoral head replaces the natural head and articulating surface of the femur. The acetabular cup replaces the natural socket and articulating surface of the acetabulum of the pelvis. In some designs, the stem and head are an integral, unitary component, but more often the stem and head are separate modular components designed to be assembled together to suit the anatomical needs of the patient.

The acetabular cup component of a total hip prosthesis is configured to be received and fixed within the acetabulum of a pelvis. The pelvis is prepared to receive the acetabular cup by reaming a concavity in the acetabular bone. The acetabular cup component typically has an outer surface conforming to the concavity reamed in the acetabular bone of the pelvis, and an inner bearing cavity for receiving the head of the femoral component. The head articulates in the bearing cavity as a ball-and-socket joint to restore motion to a defective hip joint.

One known type of acetabular cup involves an acetabular shell made of a bio-compatible metal such as titanium or a titanium alloy, and a bearing insert made of a bio-compatible polymer such as ultra-high molecular weight polyethylene. The acetabular shell is shaped generally as a hemispherical cup having a dome, or apex, at a proximal end and an annular rim at a distal end. As used herein, the words proximal and distal are terms of reference that indicate a particular portion of a prosthesis component according to the relative disposition of the portion when the component is implanted. "Proximal" indicates that portion of a component nearest the torso, whereas "distal" indicates that portion of the component farthest from the torso. Between the dome and rim, the acetabular shell comprises a shell wall defined by a generally convex proximal surface and a generally concave distal surface spaced from the proximal surface. The concave distal surface defines a shell cavity having an opening at the rim of the cup for receiving the bearing insert. The bearing insert has a generally convex proximal surface configured to be received and fixed within the acetabular shell in generally congruent engagement with the concave distal surface of the shell wall. The bearing insert also has a bearing cavity that opens distally for receiving the head of the femoral component. The bearing cavity is defined by a generally spherical concave bearing surface having a radius similar to that of the femoral head component. The concave bearing surface articulates against the surface of the spherical femoral head component.

Acetabular shells of the type described can be affixed to the acetabular bone by bone screws or bone cement. If bone screws are elected, the screws are driven into the bone through the screw holes before the bearing insert is placed into the shell. The shell also can be affixed by a combination of bone screws and bone cement. The acetabular shell can be provided with more screw holes than typically would be used by the implanting physician. This provides a selection of sites for placement of the bone screws, as may be dictated by the condition of the patient's pelvic bone or by the physician's preference.

Commonly, acetabular shells of the type described also include a dome hole at the apex. A typical dome hole is coaxially aligned with the axis of symmetry of the acetabular shell and extends through the shell wall from the concave distal surface to the convex proximal surface of the acetabular shell. Often, the dome hole is internally threaded or otherwise configured for receiving an instrument for holding and positioning the acetabular shell during implantation. Also, many physicians use the dome hole to obtain visual or tactile access to the reamed acetabular bone during implantation of the acetabular shell. Such access allows the physician to confirm that the acetabular shell is fully seated in engagement with the reamed bony surface of the acetabulum. As with the screw holes, for reasons explained below, it is also desirable to provide means for occluding the dome hole.

The bearing insert is usually designed to be received within the acetabular shell and may include locking tabs or other means for fixing the bearing insert into the shell in nonarticulating relative relationship. Nevertheless, a small amount of unintended relative motion is believed to occur between the bearing insert and the acetabular shell in response to the varying load borne by the acetabular cup during use. Such small relative motion, or micro-motion, may result in wear at the interface between the bearing insert and acetabular shell that generates fine polyethylene or metal debris. According to some hypotheses, such debris can migrate out of the acetabular cup and contact bone, possibly resulting in osteolysis, which ultimately can lead to bone resorption and possible loosening of the acetabular prosthesis.

SUMMARY OF THE INVENTION

According to one aspect of the present invention, an implantable acetabular orthopedic prosthesis includes an acetabular shell, a polyethylene bearing insert, and means, solely comprising integral portions of the shell and the insert, for permitting the insert to be assembled to the shell and for retaining the insert within the shell after assembly. The means resists push out of the bearing liner from the shell by an axially directed load of at least about 600 pounds.

DESCRIPTION OF THE PREFERRED EMBODIMENTS

Figure 6:
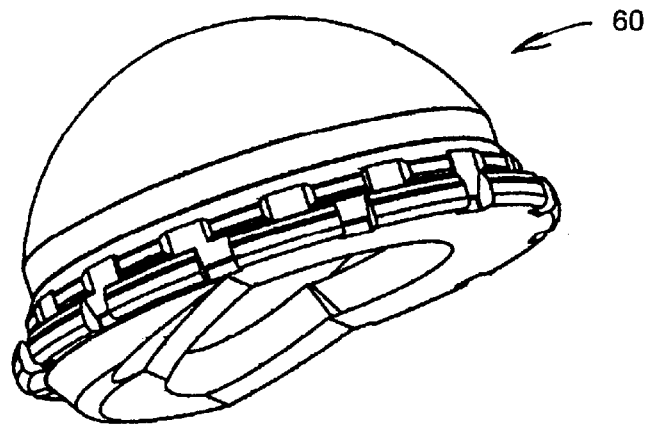
FIG. 6 is a perspective view of the bearing insert of FIG. 2.

Referring to the drawings, FIGS. 1–9, a preferred embodiment of the present invention is illustrated in the form of an implantable orthopedic prosthesis, particularly an acetabular component of a total hip joint prosthesis. The illustrated acetabular component is useful as part of that well-known type of total hip joint prosthesis that includes an acetabular component comprising an acetabular shell and an associated bearing liner, and a femoral component comprising a femoral stem and an associated spherical head. The spherical head, fixed to the femoral stem, articulates in a ball-and-socket arrangement within the bearing liner, with the bearing liner being essentially fixed within the acetabular shell. The femoral stem and acetabular shell are fixed to bone of the proximal femur and pelvic acetabulum, respectively. Only the acetabular shell and bearing liner are described in detail herein, as the various types and configurations of femoral stems and heads are well understood in the art. The illustrated acetabular shell and bearing liner are particularly resistant to disconnection and displacement from each other when implanted.

Figure 1:
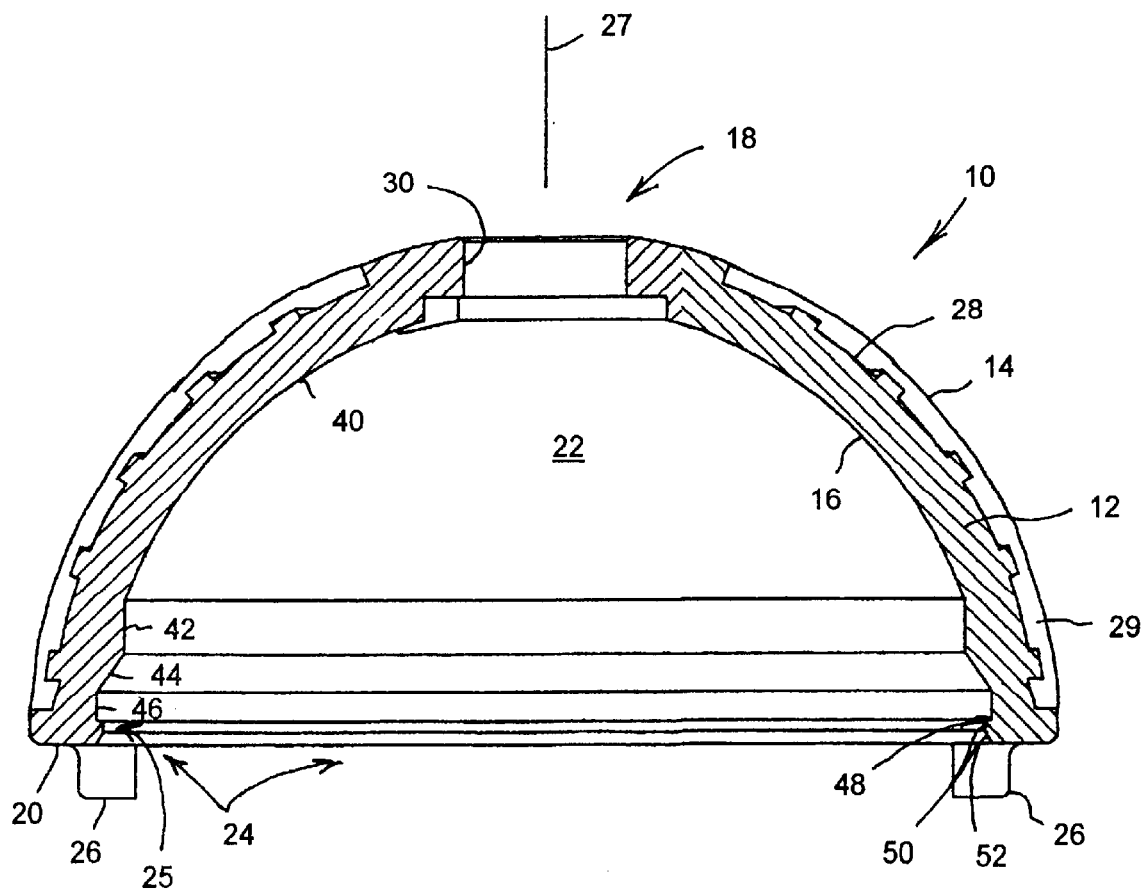
FIG. 1 is a cross-sectional view of an acetabular shell according to the present invention.

Referring to FIG. 1, an acetabular shell 10 is shown in cross-section in a plane along the axis of symmetry. Acetabular shell 10 is shaped generally as a hemispherical cup having a shell wall 12 defined by a convex proximal surface 14 and a concave distal surface 16. Acetabular shell 10 has a proximal dome region 18 at the apex of shell wall 12 and an annular rim 20 at the distal end of shell wall 12. Concave distal surface 16 of shell wall 12 defines a shell cavity 22 having an opening 24 into and through which a bearing insert, described further below, can be received. An annular lip 25 extends radially inwardly from concave distal surface 16 and, in cooperation with an annular protrusion on the bearing insert as described further below, provides a means for affixing the bearing insert against axial displacement from within shell cavity 22. Such means also includes an annular flange, described further below, on the bearing insert having notches for receiving the legs 26 that extend axially from rim 20. The interengagement of the legs 26 of shell 10 and the notches of the bearing insert flange affix the bearing insert against rotation within shell cavity 22 about the axis of symmetry 27 of acetabular shell 10 passing through the center of proximal dome region 18 at the apex of shell 10. Convex proximal surface 14 is provided with a macro-texture comprising circumferential grooves 28 filled and covered with a porous coating 29 comprised of titanium powder sintered in place. The porous coating 29 accepts the ingrowth or ongrowth of bone, and enhances adhesion of bone cement. The porous coating 29, while preferred, is not necessary for the understanding or practice of the present invention.

Referring again to FIG. 1, acetabular shell 10 includes a dome hole 30 centered in dome region 18 at the apex of shell 10 in coaxial alignment with axis 27. Dome hole 30 is internally threaded to serve as an engagement interface for an instrument (not shown) for holding and positioning acetabular shell 10 during implantation. Typically, such an instrument is used by the implanting physician to securely grasp the acetabular shell 10 and place it in the reamed acetabulum. Such an instrument usually includes an elongate handle for controlling anteversion and adduction of the acetabular shell as it is implanted, and for transmitting axial driving forces to the shell. Acetabular shell 10 can also be provided with a plurality of screw holes (not shown) through shell wall 12 between concave distal surface 16 and convex proximal surface 14. A bone screw (not shown), having a head and a threaded shank, can be inserted through a screw hole from within the shell cavity 22 and screwed into the pelvic bone underlying the acetabulum to secure acetabular shell 10 in place.

The concave distal surface 16 of shell 10, as shown in FIG. 1, starting at the dome region 18 and proceeding toward the rim 20, includes a spherical wall portion 40 followed by a first right-cylindrical wall portion 42, and a next subsequent fusty-conical wall portion 44 that slopes distally and radially outwardly. Next following fusty-conical wall portion 44 is a second right-cylindrical wall portion 46. At the distal extent of right-cylindrical wall portion 46, a shoulder 48 extends radially inwardly, followed by a third right-cylindrical wall portion 50 that extends distally therefrom, Finally, a second fusty-conical wall portion 52 slopes distally and radially outwardly from wall portion 50. Shoulder 48, right-cylindrical wall portion 50, and second fusty-conical wall portion 52 together define the annular lip 25 first mentioned above.

Figure 2:
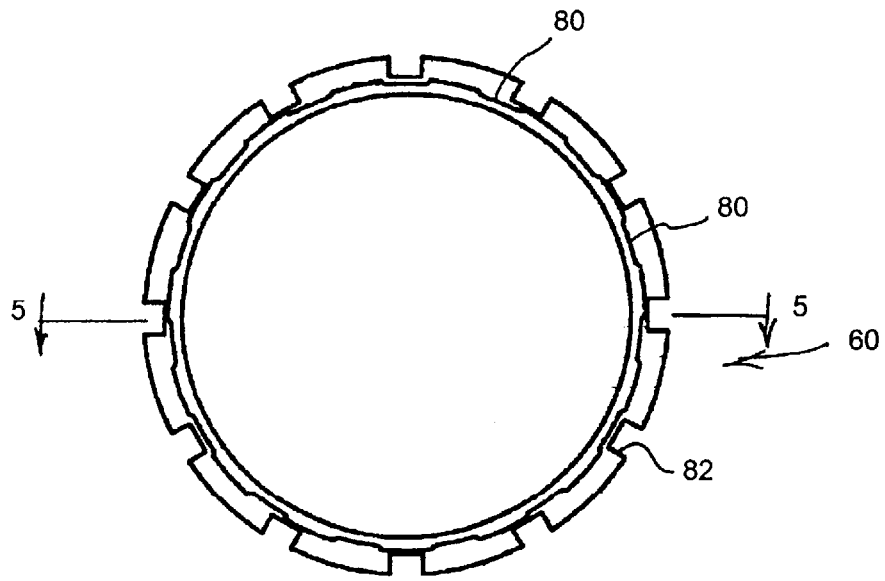
FIG. 2 is a top view of a bearing insert useful in connection with the acetabular shell of FIG. 1.
Figure 3:
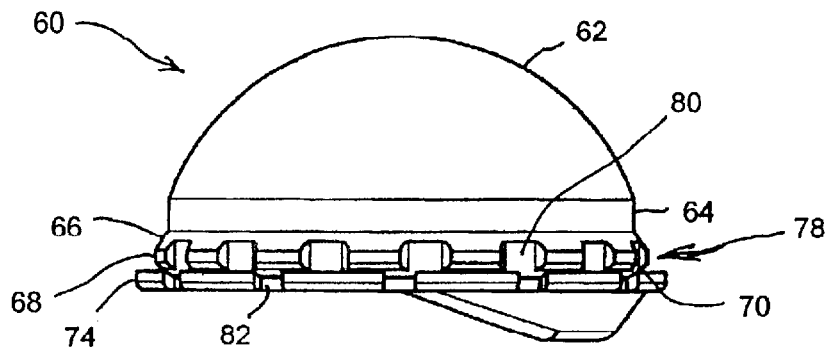
FIG. 3 is an elevational view of the bearing insert of FIG. 2.
Figure 4:
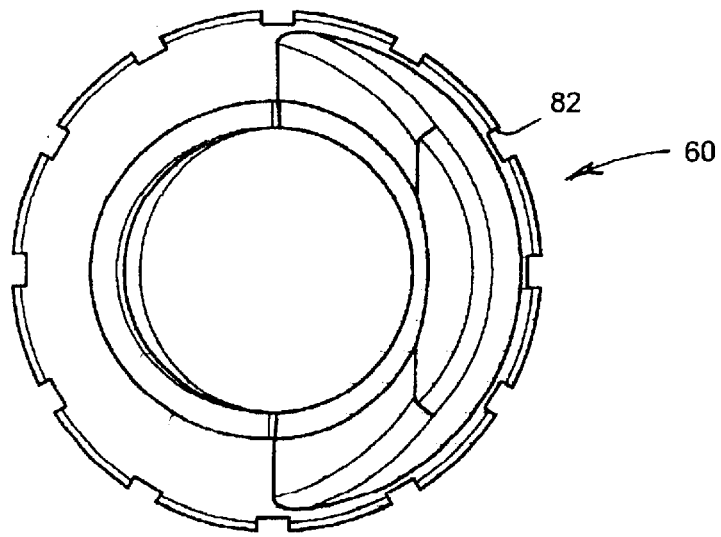
FIG. 4 is a bottom view of the bearing insert of FIG. 2.
Figure 5:
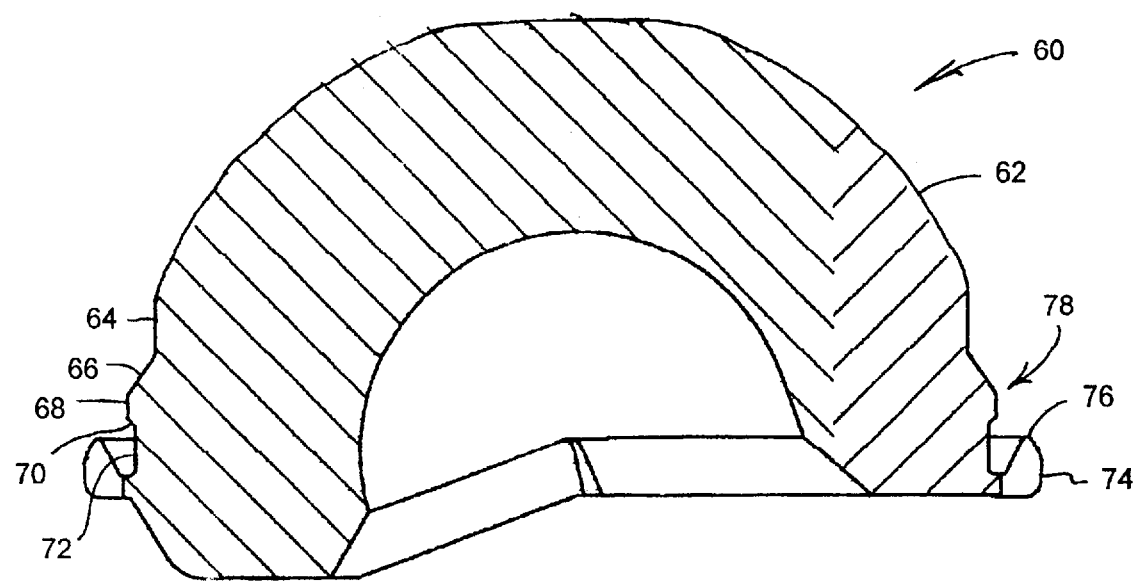
FIG. 5 is a cross-sectional view of the bearing insert of FIG. 2, taken in plane 5—5 of FIG. 2 and viewed in the direction of the arrows.

Referring to FIG. 2, 3, 4, 5 and 6, a polyethylene bearing insert 60, first mentioned above, is shown in detail. FIGS. 2, 3 and 4 are top, side and bottom views, respectively of bearing insert 60, and FIG. 5 is a cross-sectional view of the same. FIG. 6 is a perspective view of bearing insert 60. In general, bearing insert 60 is designed to fit congruently against concave distal surface 16 of acetabular shell 10, in order to minimize the opportunity for bearing insert 60 to flex under load that otherwise would be made possible by a significant gap between bearing insert 60 and acetabular shell 10. Such flexing, were it to occur, could result in micro-motion of the bearing insert 60 relative to acetabular shell 10, causing the generation of polyethylene wear debris from friction between the bearing insert 60 and the acetabular shell 10. By maintaining a high degree of congruence, the bearing insert 60 is fully supported and restrained against relative movement. To aid in maintaining congruent contact between bearing insert 60 and shell 10, bearing liner 60 is provided with an integral connection means proximate the rim thereof that engages the geometrical features of the acetabular shell 10 as described above. The connection means, while allowing ease of insertion as described further below, also results in a strong connection between bearing insert 60 and acetabular shell 10 that is highly resistant to dislocation, separation, or disengagement. Such strength of connection is highly advantageous after implantation of the acetabular component because the bearing insert is often subjected to forces by the head and femoral stem components that, under some circumstances, tend toward dislodging the bearing insert from the acetabular shell, which could result in failure of the implanted component.

Again referring to FIGS. 2–6, bearing insert 60 has includes a convex spherical wall portion 62 followed by a first right-cylindrical wall portion 64, and a next subsequent fusty-conical wall portion 66 that slopes distally and radially outwardly. Next following fusty-conical wall portion 66 is a second right-cylindrical wall portion 68. At the distal extent of right-cylindrical wall portion 68, a second fusty-conical wall portion 70 slopes distally and radially inwardly from wall portion 68, followed by a third right-cylindrical wall portion 72 that extends distally therefrom. At the distal extent of cylindrical wall portion 72, an annular rim 74 extends radially and includes a lip 76 that extends upwardly (proximally) and radially outwardly. Fusty-conical wall portion 66, cylindrical wall portion 68, and fusty-conical wall portion 70, together form an annular protrusion 78 that engages the annular groove 79 in shell 10, which is defined by fusty-conical wall surface 44, cylindrical wall surface 46, and shoulder 48 proximally of annular lip 25. As shown best in FIG. 2, annular protrusion 78 is not continuously annular, but rather is periodically relieved about its circumference by a plurality of notches 80. As preferred, about fifty percent of the circumference of annular protrusion 78 is relieved by notches 80, evenly spaced. As shown best in FIGS. 2 and 4, annular rim 74, also is not continuously annular, but rather is periodically relieved about its circumference by a plurality of notches 82. As preferred, about twenty-five percent of the circumference of annular rim 74 is relieved by notches 82, evenly spaced.

Figure 7:
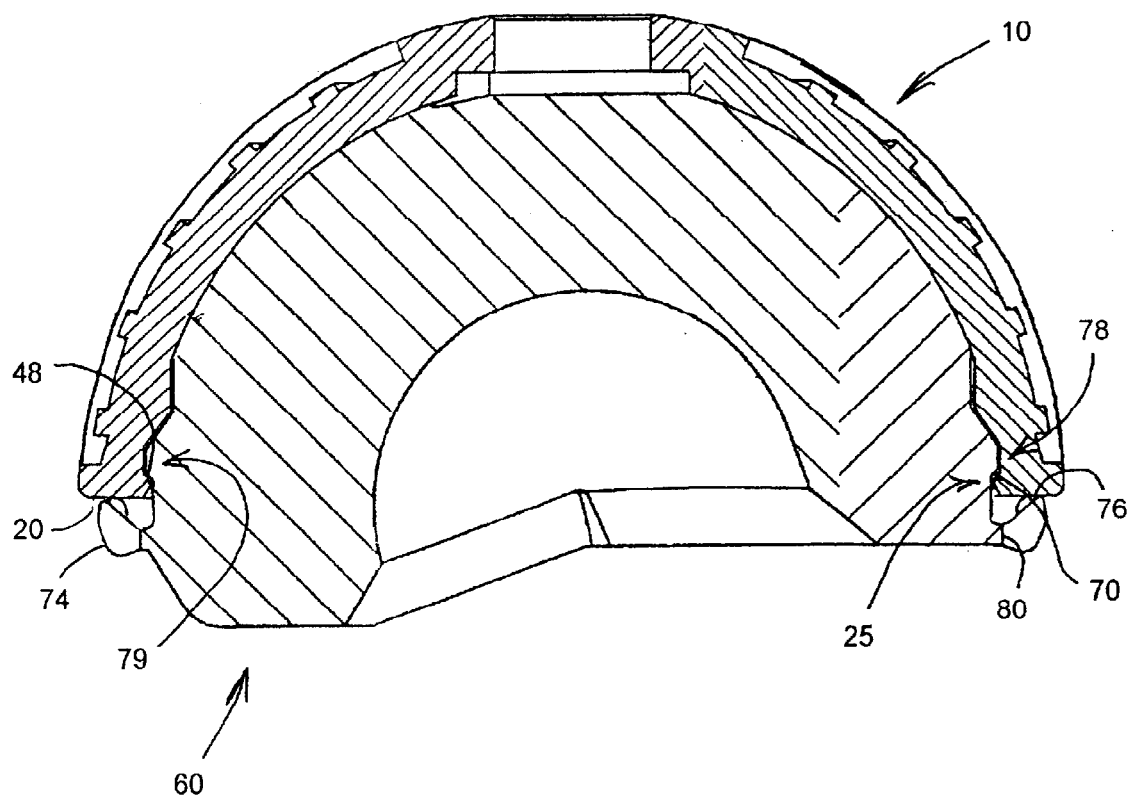
FIG. 7 is a cross-sectional view of the bearing insert of FIG. 2 assembled to the acetabular shell of FIG. 1.

Referring to FIG. 7, bearing insert 60 is shown inserted within acetabular shell 10. Fusty-conical wall portion 70 of the annular protrusion 78 of bearing insert 60 engages shoulder 48 of acetabular shell 10 to retain bearing insert 60 therein. As bearing insert 60 is inserted into acetabular shell 10, annular protrusion 78 deforms elastically, as permitted by the relieved areas 80, in order to proceed past annular lip of shell 10. Once past, annular protrusion 78 rebounds into the annular groove 79 in shell 10. Also, as bearing insert 60 is inserted into shell 10, lip 76 of annular rim 74 engages rim 20 of shell 10, and is elastically deformed distally, as permitted by relieved areas 82 and as shown best in FIG. 7. The deformed annular rim 74 maintains spring pressure against rim 20 via lip 76 to hold annular protrusion 78 tightly against shoulder 48 of shell 10.

Figures 8, 9:
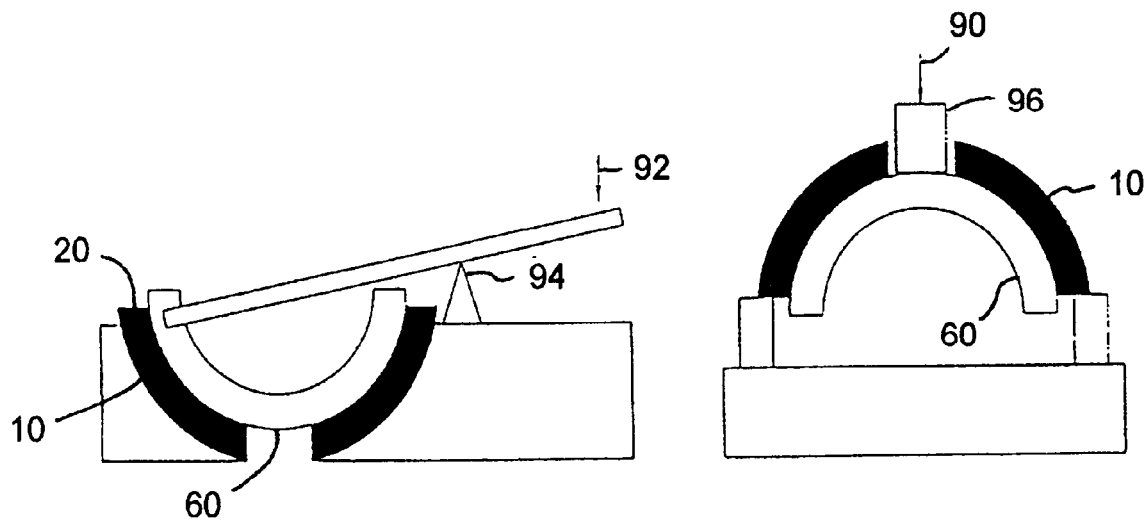
FIG. 8 is a schematic view of a test arrangement for evaluating the strength of the assembly of FIG. 7.
FIG. 9 is an alternate schematic view of a test arrangement for evaluating the strength of the assembly of FIG. 7.

Referring to FIGS. 8 and 9, a test arrangement is shown schematically, by which the resistance of bearing liner 60 against displacement from shell 10 is measured. In FIG. 8, a push out test is illustrated, whereas in FIG. 9, a lever out test is shown. By measuring the force required to dislodge bearing insert 60 from shell 10, either by an axial force 90 or a levered force 92 about a fulcrum 94 near the rim 20 of the shell, the strength of the connection between bearing insert 60 and shell 10 can be characterized.

As shown in FIG. 8, the push out test was performed on a 28 mm polyethylene insert fully seated in a 53 mm shell. The push out pin 96 was moved axially at a linear velocity of 0.2 inches per minute until failure of the insert to shell connection. An axial load of about 750 lbs was required to dislodge the bearing insert 60.

As shown in FIG. 9, the lever arm was moved about the fulcrum at an angular velocity of 1.3 radians per minute at a fulcrum located 2.2 inches from the bearing liner, until failure of the insert to shell connection. A torque load of about 580 inch-pounds was required to dislodge the bearing insert.

What is claimed is:

1. An implantable orthopedic prosthesis comprising:
   a shell having a substantially concave inner surface defining a cavity and a substantially annular groove formed therein, and also having a substantially annular circumferential rim at a distal end, wherein a plurality of legs extend from said rim; and
   a polymeric insert positionable within said cavity, said insert having a substantially annular circumferential rim with a plurality of recesses having a size such that said legs of said shell may fit within said recesses, and said insert further having a substantially convex outer surface and a circumferential protrusion projecting therefrom, said protrusion having a substantially trapezoidal cross-section wherein a first side of said trapezoid is substantially parallel to an axis of symmetry of said insert, and a second and third side of the trapezoid extend between said outer surface of said insert and said first side at an obtuse angle relative to said outer surface, a cross-section of said protrusion being substantially congruent to a cross-section of said annular groove, and said inner surface of said shell being substantially congruent with a corresponding portion of the outer surface of said insert when said insert is properly positioned within said cavity of said shell.

2. An implantable orthopedic prosthesis according to claim 1, wherein said outer surface of said insert further comprises a cylindrical wall portion that is substantially parallel to said axis of symmetry of said insert, said cylindrical wall portion being located proximally and adjacent to said circumferential protrusion.

3. An implantable orthopedic prosthesis according to claim 1, wherein said annular rim of said insert communicating with and exerting a spring force against said annular rim of said shell when said insert is properly positioned within said cavity in said shell.

4. An implantable orthopedic prosthesis according to claim 3, said protrusion having a plurality of recesses spaced along the perimeter of said insert.

5. An implantable orthopedic prosthesis according to claim 4, wherein said recesses in said protrusion are substantially equally spaced apart.

6. An implantable orthopedic prosthesis according to claim 5, wherein a distance between successive protrusions is substantially equal to a distance between successive recesses.

7. An implantable orthopedic prosthesis according to claim 4, wherein said plurality of protrusions are deformable and deform when said insert is being inserted into said shell, and return to an undeformed state when said insert is properly inserted within said shell so that said protrusions are positioned within said groove in said shell.

8. An implantable orthopedic prosthesis according to claim 1, wherein said obtuse angle between said second side of said trapezoid and said outer surface, and said obtuse angle between said third size of said trapezoid and said outer surface is between 40 and 50 degrees.

9. An implantable orthopedic prosthesis comprising:

a shell having a substantially concave inner surface and a substantially annular groove formed therein, and also having a substantially annular circumferential rim at a distal end, wherein a plurality of legs extend from said rim; and a polymeric insert positionable within said cavity, said insert having a substantially annular circumferential rim with a plurality of recesses having a size such that said legs of said shell may fit within said recesses, and said insert further having a substantially convex outer surface and a circumferential protrusion extending therefrom, said circumferential protrusion having a cross-section defined by a first surface extending radially outwardly from the outer surface of the insert and in a distal direction at an obtuse angle, a second surface adjacent said first surface and being substantially parallel to an axis of symmetry of said insert, and a third surface extending radially outwardly and in a proximal direction at an obtuse angle from said outer surface of said insert to said second surface of said circumferential protrusion, said cross-section of said protrusion being substantially congruent to a cross-section of said annular groove.

10. An implantable orthopedic prosthesis according to claim 9, wherein said outer surface of said insert further comprises a cylindrical wall portion that is substantially parallel to said axis of symmetry of said insert, said cylindrical wall portion being located proximally and adjacent to said circumferential protrusion.

11. An implantable orthopedic prosthesis according to claim 9, wherein said annular rim of said insert is deformable and communicates with and exerts a spring force against said annular rim of said shell when said insert is properly positioned within said cavity in said shell.

12. An implantable orthopedic prosthesis according to claim 11, said circumferential protrusion having a plurality of recesses spaced along the perimeter of said insert.

13. An implantable orthopedic prosthesis according to claim 12, wherein said recesses in said protrusion are substantially equally spaced apart.

14. An implantable orthopedic prosthesis according to claim 13, wherein a distance between successive protrusions is substantially equal to a distance between successive recesses.

15. An implantable orthopedic prosthesis according to claim 14, wherein said plurality of protrusions are deformable and deform when said insert is being inserted into said shell, and return to an undeformed state when said insert is properly inserted within said shell so that said inserts are positioned within said groove in said shell.

16. An implantable orthopedic prosthesis according to claim 9, wherein said obtuse angle between said outer surface of said insert and said first surface defining the cross-section of said protrusion, and said obtuse angle between said outer surface of said insert and said third surface defining the cross-section of said protrusion are between 40 and 50 degrees.

17. An implantable orthopedic prosthesis comprising:

a shell having a substantially concave inner surface defining a cavity and a substantially annular groove formed therein, and also having a substantially annular circumferential rim at a distal end, wherein a plurality of leas extend from said rim; and a polymeric insert positionable within said cavity, said insert having a substantially annular circumferential rim with a plurality of recesses having a size such that said legs of said shell may fit within said recesses, and said insert further having a substantially convex outer surface and a plurality of protrusions projecting therefrom, each of said protrusions having a substantially trapezoidal cross-section wherein at least one side of said trapezoid is substantially parallel to an axis of symmetry of said insert, a cross-section of said protrusion being substantially congruent to a cross-section of said annular groove, and said inner surface of said shell being substantially congruent with a corresponding portion of the outer surface of said insert when said insert is properly positioned within said cavity of said shell.

18. An implantable orthopedic prosthesis according to claim 17, wherein said outer surface of said insert further comprises a cylindrical wall portion that is substantially parallel to said axis of symmetry of said insert, said cylindrical wall portion being located proximally and adjacent to said circumferential protrusions.

19. An implantable orthopedic prosthesis according to claim 18, wherein said annular rim of said insert is deformable and communicates with and exerts a spring force against said annular rim of said shell when said insert is properly positioned within said cavity in said shell.

20. An implantable orthopedic prosthesis according to claim 19, wherein said protrusions are substantially equally spaced apart around a perimeter of said insert.

21. An implantable orthopedic prosthesis according to claim 18, wherein said plurality of protrusions are deformable and deform when said insert is being inserted into said shell, and return to an undeformed state when said insert is properly inserted within said shell so that said inserts are positioned within said groove in said shell.

* * * * *